United States Patent [19]
Baacke et al.

[11] Patent Number: 4,481,174
[45] Date of Patent: Nov. 6, 1984

[54] CRYSTALLINE ALUMINOSILICATE AND PROCESS FOR ITS PRODUCTION

[75] Inventors: Michael Baacke; Peter Kleinschmit, both of Hanau, Fed. Rep. of Germany

[73] Assignee: Degussa Aktiengesellschaft, Frankfurt, Fed. Rep. of Germany

[21] Appl. No.: 477,874

[22] Filed: Mar. 23, 1983

[30] Foreign Application Priority Data

Mar. 27, 1982 [DE] Fed. Rep. of Germany ....... 3211433

[51] Int. Cl.$^3$ ................. C01G 39/00; C01B 33/26
[52] U.S. Cl. .................................... 423/306; 423/328; 423/329; 502/77; 502/208; 502/232
[58] Field of Search ............. 423/328, 329, 332, 333, 423/306; 502/77, 208, 232, 240, 263

[56] References Cited

U.S. PATENT DOCUMENTS 3,947,482  3/1976  Albers et al. .......... 423/328
4,285,922  8/1981  Audeh ................... 423/329
4,427,787  1/1984  Miale et al. ............ 423/328
4,430,314  2/1984  Audeh et al. ........... 423/328

FOREIGN PATENT DOCUMENTS 42225  12/1981  European Pat. Off. ............ 423/328

OTHER PUBLICATIONS

Eugster, Science vol. 157, pp. 1177–1180, (1967).

*Primary Examiner*—Edward J. Meros
*Assistant Examiner*—Jackson Leeds
*Attorney, Agent, or Firm*—Cushman, Darby & Cushman

[57] ABSTRACT

The crystalline aluminosilicate PZ 1 is produced by carrying out the crystalline in the presence of an organic template compound of the formula $R_3P$—$(CH_2)_n$—$PR_3X_2$ where R is a lower alkyl group, n is an integer of 2 to 6 and X is $Br^-$ or $I^-$. The synthesis mixture has the composition:

| | | |
|---|---|---|
| $SiO_2/Al_2O_3$ | = | 20–250 |
| $Na_2O/SiO_2$ | = | 0.01–0.5 |
| $OH/SiO_2$ | = | 0.01–1.0 |
| $T/SiO_2$ | = | 0.01–0.2 |
| $H_2O/SiO_2$ | = | 10–40 | whereas T means template compound.

The synthesis mixture is stirred at a temperature between 90° and 200° C. at autogenous pressure. The aluminosilicate PZ 1 is changed into the aluminosilicate PZ 2 by treatment with dilute acids or with ammonium chloride and subsequent calcining. This aluminosilicate PZ 2 can be employed as catalyst in the conversion of alcohols into hydrocarbons.

14 Claims, 1 Drawing Figure

CRYSTALLINE ALUMINOSILICATE AND PROCESS FOR ITS PRODUCTION

SUMMARY OF THE INVENTION

The invention is directed to a process for the production of the new crystalline aluminosilicate PZ 1, the aluminosilicate PZ 1 itself, the production of aluminosilicate PZ 2 from aluminosilicate PZ 1, the aluminosilicate PZ 2 itself as well as the use of aluminosilicate PZ 2 as a catalyst.

The subject matter of the invention is a process for the production of the crystalline aluminosilicate PZ 1 which is characterized by carrying out the crystallization from an aqueous $SiO_2$, $Al_2O_3$ and alkali containing synthesis mixture in the presence of an organic template compound of the general formula $R_3P-(CH_2)_n-PR_3X_2$.

In the general formula $R_3P-(CH_2)_n-PR_3X_2$, R is lower alkyl, e.g. methyl, ethyl propyl and/or butyl, n is 2, 3, 4, 5, and/or 6 and X is $Br^-$ and/or $I^-$.

In a preferred illustrative form of the invention there can be employed the template compound $Bu_3P-(CH_2)_3-PBu_3Br_2$ and/or $Bu_3P-(CH_2)_3-PBu_3I_2$.

The crystallization can be carried out in a synthesis mixture which has the following composition:

| | | |
|---|---|---|
| $SiO_2/Al_2O_3$ | = | 20–250 |
| $Na_2O/SiO_2$ | = | 0.01–0.5 |
| $OH/SiO_2$ | = | 0.01–1.0 |
| $T/SiO_2$ | = | 0.01–0.2 |
| $H_2O/SiO_2$ | = | 10–40 | whereas T means template compound.

Advantageously the crystallization is carried out in such manner that the synthesis mixture is stirred at autogeneous pressure in an autoclave at a temperature between 90° and 200° C. until crystals are formed.

The aluminosilicate produced by means of the process of the invention carries the designation PZ 1. It can be characterized by its composition, its adsorption behavior, its crystal form, and its X-ray diffraction pattern.

The aluminosilicate PZ 1 has the following chemical composition:

| | |
|---|---|
| 3.0 ± 1.0% | $Na_2O$ |
| 1.5 ± 1.0% | $Al_2O_3$ |
| 85.0 ± 5.0% | $SiO_2$ |
| 0.5 ± 0.3% | $P_2O_5$ |
| 5.0 ± 3.0% | Loss on Calcining |

Scanning electron microscope photographs point to agglomerates of platelets growing together (see FIG. 1).

The X-ray diffraction pattern (Table 1) shows essentially the following lines:

TABLE 1

| d [Å] | I/Io |
|---|---|
| 15.49 | 100 |
| 9.97 | 7 |
| 9.18 | 1 |
| 7.31 | 2 |
| 5.15 | 17 |
| 4.84 | 13 |
| 4.55 | 7 |
| 4.23 | 5 |

TABLE 1-continued

| d [Å] | I/Io |
|---|---|
| 3.68 | 6 |
| 3.56 | 14 |
| 3.44 | 59 |
| 3.30 | 30 |
| 3.15 | 28 |
| 2.15 | 18 |
| 1.88 | 3 |
| 1.83 | 6 |

It was measured according to standard methods with a scintillation counter-diffractometer with $CuK\alpha$ radiation. d[Å] designates the interplanary distances and I/Io their relative intensities.

Adsorption measurements (20° C., 50% relative humidity lead to the following results (data in grams of adsorbed substance per gram of silicate):

| | |
|---|---|
| n-hexane | 0.01 |
| benzene | 0.03 |
| water | 0.07 |

If the aluminosilicate PZ 1 is treated with a dilute acid, preferably a mineral acid, as for example sulfuric acid or hydrochloric acid or subjected to an ion exchange with $NH_4Cl$ and subsequent calcinization, then there is formed a new crystalline aluminosilicate PZ 2, whose X-ray diffraction pattern (Table 2) shows a change in structure.

TABLE 2

| d [Å] | I/Io |
|---|---|
| 13.48 | 100 |
| 7.34 | 24 |
| 3.55 | 55 |
| 3.40 | 85 |
| 1.85 | 20 |

Scanning electron microscope photographs on the contrary do not detect any change in crystal form or size in the passage PZ 1→PZ 2.

The aluminosilicate PZ 2 has the following analytical composition:

| | |
|---|---|
| 0.05 ± 0.03% | $Na_2O$ |
| 1.40 ± 0.6% | $Al_2O_3$ |
| 88.0 ± 3.0% | $SiO_2$ |
| 0.5 ± 0.2% | $P_2O_5$ |
| 3.0 ± 1.0% | Loss on Ignition |

Adsorption experiments at 20° C. and 50% relative humidity led to the following results:

| | |
|---|---|
| n-hexane | 0.06 |
| benzene | 0.04 |
| water | 0.05 |

(data in grams of adsorbed substance per gram of silicate).

The aluminosilicate PZ 2 is suitable for use as a catalyst, especially for converting alcohols into hydrocarbons, e.g. converting an alkanol such as methanol or ethanol to a hydrocarbon mixture rich in olefins at a temperature of 400° C. Generally there can be used the conditions and temperature ranges employed with zeolite ZSM 5 in converting lower alcohols to hydrocarbon mixtures as described by Meisel et al., Chemtech 6, 86 (1976)

From the literature (H. P. Eugster, Science Vol. 157, pages 1177-1180 (1967) there is known a mineral layered silicate whose X-ray diffraction pattern is similar to that of PZ 1. However, there are exhibited clear differences at many interplanar distances.

The mineral layered silicate, magadiite, is described as sodium silicate hydrate of the formula $NaSi_7O_{13}(OH)_3 3H_2O$, while for the crystallization of PZ 1 an aluminum compound must be present. Upon increasing the $SiO_2/Al_2O_3$ ratio above about 250:1 there is no longer obtained PZ 1 but another product.

In the same literature there is also described the conversion of magadiite into a compound SH whose X-ray diffraction pattern is similar to that of PZ 2, but likewise exhibits clear differences. Besides in the above-mentioned literature there is expressly described the conversion of SH into magadiite by treating with $Na_2CO_3$ or NaOH. In the treatment of PZ 2 with these compounds to be sure analytically a sodium absorption is detected but there is no structured change PZ 2→PZ1 as can be readily detected by the adsorption of the X-ray diffraction pattern. From Audeh U.S. Pat. No. 4,285,922 there is known the production of a nonidentified material as byproduct in the crystallization of ZSM 5 which exhibits an X-ray diffraction pattern similar to PZ 1. However, this material 3 forms preferably at $SiO_2/Al_2O_3$ ratios which are greater than 500:1, and at least are greater than 300:1. PZ 1 on the contary exists at mole ratios between about 50 and about 250:1. A further decisive difference is in the behavior in ion exchange. The X-ray diffraction pattern given in Audeh U.S. Pat. No. 4,285,922 is characteristic for all products obtained through ion exchange, while with PZ 1 in the ion exchange, for example, with $NH_4Cl$, there is a rearrangement to PZ 2, for which there can be observed a changed X-ray diffraction pattern.

Unless otherwise indicated all parts and percentages are by weight.

The processes can comprise, consist essentially of, or consist of the stated steps with the recited materials.

EXAMPLE 1

2.4 grams of alumina trihydrate were dissolved in 50 ml of a 6.2N NaOH solution and added to a suspension of 120 grams of precipitated silica (89% $SiO_2$) in a solution of 25 grams of $Bu_3P—(CH_2)_3—PBu_3Br_2$ in 750 ml of water. This mixture was stirred for 20 minutes at 50° C., transferred into a steel autoclave and stirred for 310 hours at 100° C. After the end of the crystallization the crystals were separated off by filtration, washed with water and dried for 12 hours at 120° C.

EXAMPLE 2

The procedure was analogous to Example 1 but in place of alumina trihydrate there was employed the same amount of sodium aluminate, the amount of NaOH reduced to 3.5 grams and stirring was for 200 hours at 130° C.

EXAMPLE 3

In this example in distinction from Example 1 there were used 4.2 grams of alumina trihydrate, 16.5 grams of NaOH and 100 grams of precipitated silica and stirring was for 50 hours at 160° C.

EXAMPLE 4

The amounts employed were:

| | |
|---|---|
| Alumina trihydrate | 6.5 grams |
| NaOH | 25 grams |
| Precipitated silica | 310 grams |
| $Bu_3P—(CH_2)_3—PBu_3Br_2$ | 60 grams |
| $H_2O$ | 2500 ml |

It was crystallized for 14 hours at 175° C.

In Examples 1 to 4 there were obtained well crystallized aluminosilicate PZ 1.

EXAMPLE 5

50 grams of PZ 1 from Example 2 were stirred in 500 ml of 1N HCl for 2 hours at 80° C., filtered off, washed with water until neutral and dried for 17 hours at 120° C.

EXAMPLE 6

30 grams of PZ 1 from Example 2 were stirred for 2 hours at 80° C. with 300 ml of 5N $NH_4Cl$ solution, filtered off, washed with water until $Cl^-$ free, dried for 4 hours at 120° C. and calcined for 16 hours at 550° C.

Examples 5 and 6 gave well crystallized aluminosilicate PZ 2.

What is claimed is:

1. A process for the production of crystalline aluminosilicate PZ 1 having analytical composition:

| | |
|---|---|
| 3.0 ± 1.0% | $Na_2O$ |
| 1.5 ± 1.0% | $Al_2O_3$ |
| 85.0 ± 5.0% | $SiO_2$ |
| 0.5 ± 0.3% | $P_2O_5$ |
| 5.0 ± 3.0% | Loss on Calcining | and an X-ray diffraction pattern having the following lines:

| d [Å] | I/Io |
|---|---|
| 15.49 | 100 |
| 9.97 | 7 |
| 9.18 | 1 |
| 7.31 | 2 |
| 5.15 | 17 |
| 4.84 | 13 |
| 4.55 | 7 |
| 4.23 | 5 |
| 3.68 | 6 |
| 3.56 | 14 |
| 3.44 | 59 |
| 3.30 | 30 |
| 3.15 | 28 |
| 2.15 | 18 |
| 1.88 | 3 |
| 1.83 | 6 | comprising crystallizing said aluminosilicate from an aqueous $SiO_2$, $Al_2O_3$ and an alkali containing synthesis mixture having a composition as follows:

| | | |
|---|---|---|
| $SiO_2/Al_2O_3$ | = | 20-250 |
| $Na_2O/SiO_2$ | = | 0.01-0.5 |
| $OH/SiO_2$ | = | 0.01-1.0 |
| $T/SiO_2$ | = | 0.01-0.2 |
| $H_2O/SiO_2$ | = | 10-40 | wherein T is an organic template compound of the formula $R_3P-(CH_2)_n-PR_3X_2$ wherein R is a lower alkyl group, n is an integer from 2 to 6 and X is $Br^-$ or $I^-$.

2. A process according to claim 1 where R is methyl, ethyl, propyl, or butyl.

3. A process according to claim 2 wherein R is butyl and n is 3.

4. A process accordng to claim 1 where R is butyl.

5. A process according to claim 4 comprising stirring the synthesis mixture at a temperature between 90° and 200° C. at autogeneous pressure until the crystals are formed.

6. A process according to claim 1 comprising stirring the synthesis mixture at a temperature between 90° and 200° C. at autogenous pressure until the crystals are formed.

7. A crystalline aluminosilicate selected from the group consisting of (1) aluminosilicate PZ1 having analytical composition:

| | |
|---|---|
| 3.0 ± 1.0% | $Na_2O$ |
| 1.5 ± 1.0% | $Al_2O_3$ |
| 88.0 ± 5.0% | $SiO_2$ |
| 0.5 ± 0.3% | $P_2O_5$ |
| 5.0 ± 3.0% | Loss on Calcining | and an X-ray diffraction pattern having the following lines:

| d [Å] | I/Io |
|---|---|
| 15.49 | 100 |
| 9.97 | 7 |
| 9.18 | 1 |
| 7.31 | 2 |
| 5.15 | 17 |
| 4.84 | 13 |
| 4.55 | 7 |
| 4.23 | 5 |
| 3.68 | 6 |
| 3.56 | 14 |
| 3.44 | 59 |

-continued

| d [Å] | I/Io |
|---|---|
| 3.30 | 30 |
| 3.15 | 28 |
| 2.15 | 18 |
| 1.88 | 3 |
| 1.83 | 6 | and (2) aluminosilicate PZ2

| | |
|---|---|
| 0.05 ± 0.03% | $Na_2O$ |
| 1.40 ± 0.6% | $Al_2O_3$ |
| 88.0 ± 3.0% | $SiO_2$ |
| 0.5 ± 0.2% | $P_2O_5$ |
| 3.0 ± 1.0% | Loss on Ignition | and an X-ray diffraction pattern having the following lines

| d [Å] | I/Io |
|---|---|
| 13.48 | 100 |
| 7.34 | 24 |
| 3.55 | 55 |
| 3.40 | 85 |
| 1.85 | 20. |

8. A compound according to claim 7 which is aluminosilicate PZ 1.

9. A compound according to claim 7 which is aluminosilicate PZ 2.

10. A process for preparing the aluminosilicate PZ 2 of claim 9 comprising treating aluminosilicate PZ 1 with dilute acid.

11. A process according to claim 10 wherein the acid is mineral acid.

12. A process according to claim 11 wherein the mineral acid is sulfuric acid or hydrochloric acid.

13. A process according to claim 12 wherein the mineral acid is hydrochloric acid.

14. A process of preparing the aluminosilicate PZ 2 of claim 9 comprising subjecting aluminosilicate PZ 1 to ion exchange with $NH_4Cl$ and when calcining the ion exchanged product.

* * * * *